United States Patent
Yun et al.

(10) Patent No.: US 10,635,868 B1
(45) Date of Patent: Apr. 28, 2020

(54) SENSOR SYSTEM USING STRETCHABLE ANTENNA

(71) Applicants: Samsung Electronics Co., Ltd., Suwon-si, Gyeonggi-do (KR); THE BOARD OF TRUSTEES OF THE LELAND STANFORD JUNIOR UNIVERSITY, Stanford, CA (US)

(72) Inventors: Youngjun Yun, Yongin-si (KR); Naoji Matsuhisa, Stanford, CA (US); Simiao Niu, Stanford, CA (US); Zhenan Bao, Stanford, CA (US); William Burnett, Stanford, CA (US)

(73) Assignees: Samsung Electronics Co., Ltd., Gyeonggi-do (KR); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/244,225

(22) Filed: Jan. 10, 2019

(51) Int. Cl.
| | |
|---|---|
| *G06K 7/08* | (2006.01) |
| *G06K 7/10* | (2006.01) |
| *G06K 19/07* | (2006.01) |
| *G06K 19/077* | (2006.01) |
| *H01Q 1/22* | (2006.01) |
| *H01Q 7/00* | (2006.01) |

(52) U.S. Cl.
CPC ..... *G06K 7/10366* (2013.01); *G06K 19/0723* (2013.01); *G06K 19/07777* (2013.01); *H01Q 1/2225* (2013.01); *H01Q 7/00* (2013.01)

(58) Field of Classification Search
CPC ...... G06K 7/0008; G06F 3/1454; G06F 3/147
USPC ........................................ 235/451
See application file for complete search history.

(56) References Cited

U.S. PATENT DOCUMENTS 9,945,739 B2   4/2018 Jeon et al.
10,080,524 B1 * 9/2018 Xi ........................ A61B 5/4842
(Continued)

FOREIGN PATENT DOCUMENTS

KR    10-1048506 B1   7/2011
KR    20170023026 A   3/2017
(Continued)

OTHER PUBLICATIONS

Xu et. al 'Soft Microfluidic Assemblies of Sensors, Circuits, and Radios for the Skin' Science Apr. 4, 2014, vol. 344, Issue 6179, pp. 70-74.
(Continued)

*Primary Examiner* — Ahshik Kim
(74) *Attorney, Agent, or Firm* — Harness, Dickey & Pierce, P.L.C.

(57) ABSTRACT

An example embodiment provides a sensor system including a tag unit and a readout unit. The tag unit includes a first sensor having a stretchable antenna and a stretchable resistor. The tag unit may be configured to create a sensing signal corresponding to a degree of stretching of the stretchable resistor, transmit the sensing signal to the readout unit through the stretchable antenna, and operate in a first region corresponding to a first frequency. The readout unit may be inductively coupled to the tag unit and may be configured to receive and read out the sensing signal, and operate in a second region corresponding to a second frequency. The first frequency may range 30 MHz to 50 MHz, and the second frequency may be different from the first frequency.

20 Claims, 17 Drawing Sheets

(56) References Cited

U.S. PATENT DOCUMENTS

| | | | |
|---|---|---|---|
| 2013/0341411 A1* | 12/2013 | Kai .................. | G06K 19/07783 |
| | | | 235/492 |
| 2014/0035728 A1* | 2/2014 | Lee .................... | G06K 7/10198 |
| | | | 340/10.1 |
| 2014/0095102 A1* | 4/2014 | Potyrailo ............... | G01R 27/28 |
| | | | 702/127 |
| 2016/0006123 A1 | 1/2016 | Li et al. | |
| 2016/0028153 A1 | 1/2016 | Li et al. | |
| 2016/0328537 A1 | 11/2016 | Viikari | |
| 2017/0150896 A9 | 6/2017 | Lu et al. | |
| 2017/0182330 A1 | 6/2017 | Schneider et al. | |
| 2017/0202467 A1 | 7/2017 | Zitnik et al. | |

FOREIGN PATENT DOCUMENTS

| | | |
|---|---|---|
| KR | 20170044826 A | 4/2017 |
| KR | 20170058524 A | 5/2017 |
| KR | 10-1811214 B1 | 12/2017 |

OTHER PUBLICATIONS

Huang et. al. 'Materials and Designs for Wireless Epidermal Sensors of Hydration and Strain' Adv. Funct. Mater. 2014, 24, 3846-3854.

Kim et. al. 'Battery-free, stretchable optoelectronic systems for wireless optical characterization of the skin' Sci. Adv. Aug. 3, 2016, 2:e1600418.

Extended European Search Report dated Nov. 25, 2010, issued in corresponding European Patent Application No. 19169709.3.

\* cited by examiner

SENSOR SYSTEM USING STRETCHABLE ANTENNA

BACKGROUND

(a) Field

Inventive concepts relate to a sensor system, and more particularly, to a sensor system using a stretchable antenna.

(b) Description of Related Art

A skin-attached sensor system in the related art may be configured by forming a sensor unit on a stretchable substrate made of a rubber material and mounting a rigid circuit unit on the substrate made of a rubber material. A sensor and a signal processing circuit of the sensor system in the related art may be connected to each other through a wire formed in a wavy shape so that the wire is stretchable.

In addition, in the case of another sensor system in the related art, an antenna, which enables wireless communication, may be further mounted on the sensor unit, such that the sensor system may be configured as a system that reads out, from the outside, a signal measured by the sensor.

In addition, in the case of still another sensor system in the related art, an antenna may be connected to a stretchable sensor, such that the sensor system may be configured as a system capable of reading out, from the outside, a variation in resonant frequency corresponding to a degree of stretching of the sensor.

Even though the sensor system in the related art may be attached to skin, the sensor system in the related art may be bulky and uncomfortable, which limits implementing as a flexible/stretchable electronic device, and may require a separate battery to operate ICs and the like.

In addition, another sensor system in the related art may read out, from the outside, a signal by using wireless communication but cannot use a commercially available NFC frequency (13.56 MHz), and as a result, the sensor system may not be compatible with currently used mobile phones and the like, and the sensor system may be vulnerable to frequency modulation according to a degree of stretching of the sensor because the sensor system is a system that receives resonant frequency modulation.

In addition, in the case of still another sensor system in the related art, the wearing comfort may be poor because of a rigid circuit unit that is embedded.

The above information disclosed in this Background section is only for enhancement of understanding of relevant art and therefore may contain information that does not form the prior art that is already known in this country to a person of ordinary skill in the art.

SUMMARY

Inventive concepts relate to a sensor system that includes a tag having an antenna that has a small volume and does not require a separate battery.

Inventive concepts also relate to a sensor system capable of using a commercially available NFC frequency (13.56 MHz).

Inventive concepts also relate to a sensor system that is attachable to the skin and includes a stretchable tag with improved wearing comfort.

Technical features and effects of inventive concepts are not limited to those discussed above, and other features and/or effects of inventive concepts may be understood by those skilled in the art from the following description of the presented embodiments.

According to an embodiment of inventive concepts, a sensor system may include a tag unit and a readout unit. The tag unit may include a first sensor, which may include a stretchable antenna and a stretchable resistor. The tag unit may be configured to create a sensing signal corresponding to a degree of stretching of the stretchable resistor, transmit the sensing signal to the readout unit through the stretchable antenna, and operate in a first region corresponding to a first frequency. The readout unit may be inductively coupled to the tag unit. The readout unit may be configured to receive and read out the sensing signal, and operate in a second region corresponding to a second frequency. The first frequency may range from 30 MHz to 50 MHz, and the second frequency may be different from the first frequency.

In some embodiments, the second frequency may be 13.56 MHz, the first region may be a region corresponding to the first frequency and a first coupling coefficient, the second region may be a region corresponding to the second frequency and a second coupling coefficient, and the first coupling coefficient may be greater than the second coupling coefficient.

In some embodiments, the stretchable antenna may include stretchable electrodes that form an inductor and a first capacitor. The stretchable electrodes may include a first stretchable electrode and a second stretchable electrode. The second stretchable electrode may overlap a apart of the inductor. The inductor may include the first stretchable electrode. The inductor may have a spiral shape, wherein the first stretchable electrode may be arranged in the spiral shape. The capacitor may include the second stretchable electrode. The inductor and the capacitor may be configured to be stretched from a first state to a second state that is different than the first state.

In some embodiments, in the second state, a resistance value of the first stretchable electrode may be a first reference resistance value or less, and a resistance value of the second stretchable electrode may be a second reference resistance value or less.

In some embodiments, in the first state, a resistance value of the stretchable resistor may be a third reference resistance value or less.

In some embodiments, the first reference resistance value, the second reference resistance value, and the third reference resistance value may be 100Ω, 3Ω, and 1,000Ω, respectively.

In some embodiments, the first capacitor may have a sandwich structure in which a dielectric material is included between a part of the inductor and the second stretchable electrode, and a conductivity of each of the first stretchable electrode and the second stretchable electrode may be lower than 0.05 Ohm/square.

In some embodiments, the sandwich structure may include two SEBS dielectric materials.

In some embodiments, the inductor may have inductance of 451.5 nH and a resistance value of 2.98 Ω in the first state, and may have an inductance of 595.2 nH and a resistance value of 41.7Ω in the second state.

In some embodiments, a unit capacitance of the first capacitor may be 16.3 pF/cm$^2$ in the first state and 22.0 pF/cm$^2$ in the second state.

In addition, in the sensor system according to an example embodiment, the first sensor may be a resistive strain sensor attachable to skin and made of a nano-oxygen tube material.

In some embodiments, the first state may be a non-stretched state, and the second state may be a state further stretched by 50% than the first state.

In some embodiments, the stretchable antenna may further include a diode, a second capacitor, and a first ring oscillator having a first operating frequency range. The diode may be configured to rectify a wireless power signal corresponding to the second region to provide a rectified wireless power signal. The second capacitor may be configured to store energy corresponding to the rectified wireless power signal. The first ring oscillator may be configured to operate by using energy stored in the second capacitor and create a first modulated sensing signal by modulating a frequency of the sensing signal in accordance with the degree of stretching of the first sensor within the first operating frequency range, and the readout unit may be configured to read out the first modulated sensing signal.

In some embodiments, the antenna may further include a second sensor, and a second ring oscillator having a second operating frequency range. The second ring oscillator may be configured to create a second modulated sensing signal by modulating a frequency of the sensing signal in accordance with a degree of stretching of the second sensor within the second operating frequency range. The first sensor and the first ring oscillator may match with each other. The second sensor and the second ring oscillator may match with each other, and the first operating frequency range and the second operating frequency range may be different from each other.

In some embodiments, the readout unit may be configured to distinguish and read out the first modulated sensing signal and the second modulated sensing signal.

In some embodiments, the readout unit may include a first band-pass filter corresponding to the first operating frequency range, and a second band-pass filter corresponding to the second operating frequency range, and may be configured to distinguish and read out the first modulated sensing signal and the second modulated sensing signal by using the first band-pass filter and the second band-pass filter.

In some embodiments, the diode may have a metal-semiconductor Schottky structure.

In some embodiments, the second reference resistance value may be greater than the first reference resistance value and less than the third reference resistance value.

In some embodiments, the first state may be a non-stretched state and the second state may be a stretched state. The inductor may have a first inductance value and a first resistance value in the first state, and the inductor may have a second inductance value and a second resistance value in the second state. The second inductance value may be greater than the first inductance value, and the second resistance value may be greater than the first resistance value.

In some embodiments, the second capacitor, the second sensor, the first ring oscillator, and the second ring oscillator may be made of stretchable materials.

According to inventive concepts, a sensor system includes a tag having an antenna that has a small volume and does not require a separate battery.

In addition, according to inventive concepts, a sensor system capable of using a commercially available NFC frequency (13.56 MHz) is provided.

In addition, according to inventive concepts, a sensor system is attachable to the skin and includes a stretchable tag with improved wearing comfort.

DETAILED DESCRIPTION

Figure 1:
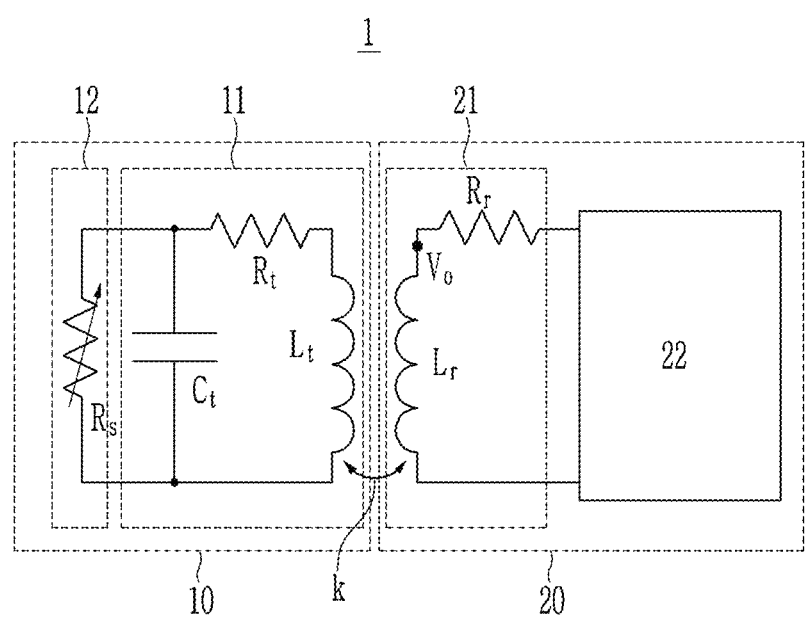
FIG. 1 is a block diagram of a sensor system according to an example embodiment.

Hereinafter, some example embodiments will be described in detail with reference to the accompanying drawings. Identical or similar constituent elements will be designated by identical reference numerals, and a repeated description thereof will be omitted. In addition, the suffixes "module" and "part" of constituent elements used in the description below are assigned or used only in consideration of the ease of writing the specification and do not have meanings or roles distinguished from each other. In addition, in the description, the specific descriptions of publicly known related technologies will be omitted when it is determined that the specific descriptions may obscure the subject matters of example embodiments disclosed in the present specification. In addition, it should be interpreted that the accompanying drawings are provided only to allow those skilled in the art to easily understand example embodiments disclosed in the present specification, and the technical spirit disclosed in the present specification is not limited by the accompanying drawings, and includes all alterations, equivalents, and alternatives that are included in the spirit and the technical scope of inventive concepts.

Terms including ordinal numerals such as "first", "second", and the like may be used to describe various constituent elements, but the constituent elements are not limited by these terms. These terms are used only to distinguish one constituent element from another constituent element.

When one constituent element is described as being "connected" or "linked" to another constituent element, it should be understood that one constituent element can be connected or linked directly to another constituent element, and an intervening constituent element can also be present between the constituent elements. On the other hand, when it is mentioned that a certain element is "directly connected" or "directly linked" to another element, it should be understood that other elements do not exist therebetween.

Singular expressions used herein include plural expressions unless they have definitely opposite meanings in the context.

In the present application, it should be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

Hereinafter, a sensor system according to an example embodiment will be described with reference to FIG. 1.

A sensor system 1 according to an example embodiment includes a skin-attached stretchable tag unit 10 (hereinafter, referred to as the tag unit) and a stretchable readout unit 20 (hereinafter, referred to as the readout unit), and the tag unit 10 and the readout unit 20 are coupled to each other in an inductive-coupling manner by using a desired (and/or alternatively predetermined) resonant frequency f (e.g., 13.5 Mhz).

The tag unit 10 and the readout unit 20 may communicate with each other by using, but not limited to, wireless communication such as NFC or RFID.

The readout unit 20 supplies driving power to the tag unit 10 in a contactless manner through a wireless power signal and receives and reads out, in an amplitude modulation and signal detection manner, a sensing signal created by the tag unit 10. Specifically, the readout unit 20 including an antenna 21 and a circuit unit 22 is attachable to a user's clothing and reads out the sensing signal of the tag unit 10 by using amplitude of an output voltage Vo obtained from the antenna 21.

The antenna 21 may be represented as an equivalent circuit including a stretchable inductor (hereinafter, referred to as the inductor) Lr and a parasitic resistor Rr which are connected to each other in series, and the circuit unit 22 reads out the sensing signal made by the amplitude modulation.

Three parameters, a resonant frequency f, a quality factor Q, and a coupling coefficient k are present between the tag unit 10 and the readout unit 20, and the resonant frequency f and the quality factor Q may be represented by the following Equation 1.

$$Q = \frac{2\pi f L_{tag}}{R_{tag}}, f = \frac{1}{2\pi\sqrt{L_{tag}C_{tag}}}$$ [Equation 1]

Here, $L_{tag}$, $C_{tag}$, and $R_{tag}$ may be values of inductance, capacitance, and parasitic resistance of an antenna 11, respectively.

The tag unit 10 includes the stretchable antenna 11 (hereinafter, referred to as the antenna) and a stretchable sensor 12 (hereinafter, referred to as the sensor), creates the sensing signal by loading modulation in accordance with a change in resistance value corresponding to the degree of stretching of a stretchable resistor Rs (see FIG. 6, hereinafter, referred to as the resistor) included in the sensor 12, and may transmit the sensing signal to the readout unit 20 through the antenna 11.

The antenna 11 may be represented as an equivalent circuit including an inductor Lt, a stretchable capacitor (hereinafter, referred to as the capacitor) Ct, and a parasitic resistor Rt which may be connected to one another in parallel.

Figure 2A:
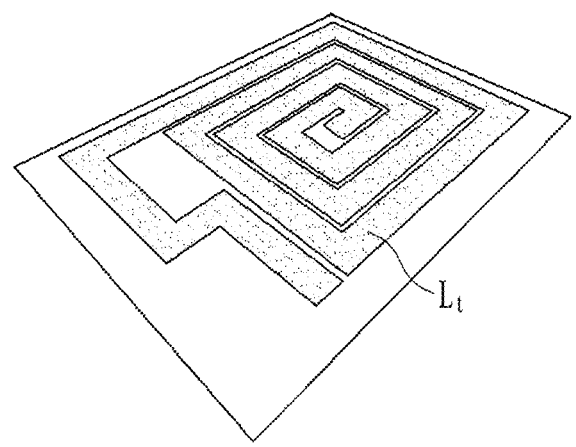
FIG. 2A is a view illustrating a shape of an antenna according to an example embodiment.
Figure 2B:
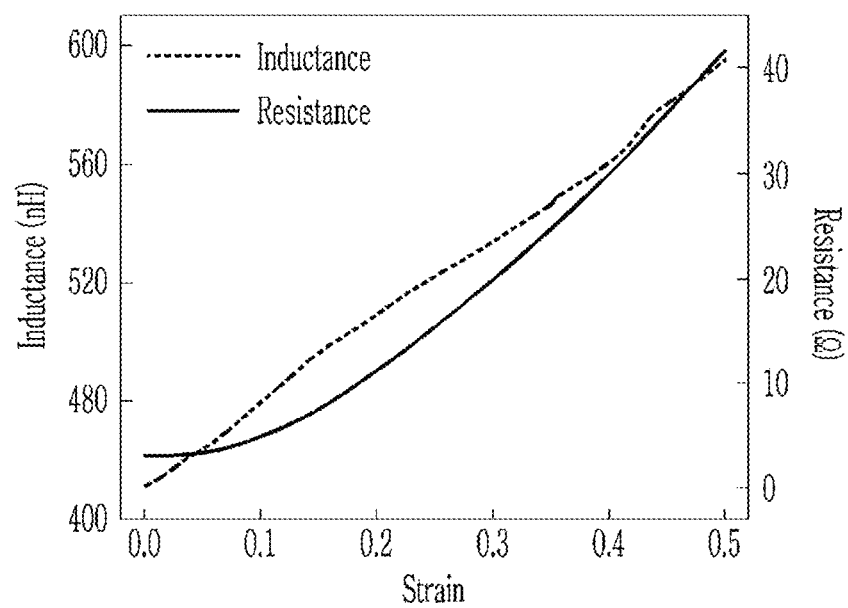
FIG. 2B is a graph illustrating inductance characteristics of the antenna according to an example embodiment.

Hereinafter, an example of the inductor Lt according will be described with reference to FIGS. 2A and 2B. FIG. 2A is a view illustrating a shape of the antenna according to an example embodiment, and FIG. 2B is a graph illustrating inductance characteristics of the antenna according to an example embodiment.

Referring to FIG. 2A, the antenna 11 may be formed in a spiral shape by winding a stretchable electric conductor in a desired (and/or alternatively predetermined) direction (e.g., counterclockwise), and the stretchable electric conductor having a wound shape may form the inductor Lt that has been described with reference to FIG. 1. For example, the stretchable electric conductor may be manufactured by embedding stretchable Ag nanoparticles having high conductivity in polyurethane PU, and the conductivity of the stretchable electric conductor may have a value less than 0.5 Ohm/square, is but not limited to.

In some embodiments, the inductor Lt may need to have an inductance higher than 100 nH in order to provide sufficient sensitivity S (see FIG. 5B) and an internal resistance may be a first reference resistance value of about 100Ω or less.

Hereinafter, an example of a method of manufacturing the inductor Lt will be described.

First, stretchable conductive ink (e.g., composite ink of flakes and elastomers, PE873) may be printed in a spiral shape on a stretchable electrode (hereinafter, referred to as the stretchable electrode), such as a styrene-ethylene-butylene-styrene (SEBS) electrode, by stencil printing or dispenser printing. For example, a printer (e.g., Voltera V-one) may be used, and the SEBS substrate may be characterized by a high yield voltage, excellent dielectric leakage, and high stretchability, and may be an SEBS substrate of 10 μm H1221.

The spiral inductor having a size of 4.9 cm*4.5 cm may be formed by rotating four times in order to reach a desired inductance. A wide line (e.g., a width of 4 mm) may be designed to reduce and/or minimize a ratio between an overall spiral length and the width, thereby reducing internal resistance of the inductor in order to increase a value of the quality factor Q. In this case, a pattern of the inductor Lt may be designed by using, but not limited to, Altium Designer software.

Next, the printed conductor ink is completely cured by performing annealing at 105° C. for 30 minutes.

Referring to FIG. 2B, in a first state (e.g., the inductor Lt is not stretched so the strain is 0), the inductor Lt has inductance of 451.5 nH, and a resistance value of the parasitic resistor Rt caused by the inductor Lt is 2.98Ω. In a second state, where the inductor Lt is stretched about 50% to a strain value of about 0.5, the inductance may increase by 31.8% to 595.2 nH, and the resistance value may increase by about 14 times to 41.7Ω. In this case, the resistance value of the parasitic resistor Rt is still the first reference resistance value (100Ω) or less, and as a result, it is possible to successfully operate the system 1 even under a highly stretched condition.

Figure 3A:
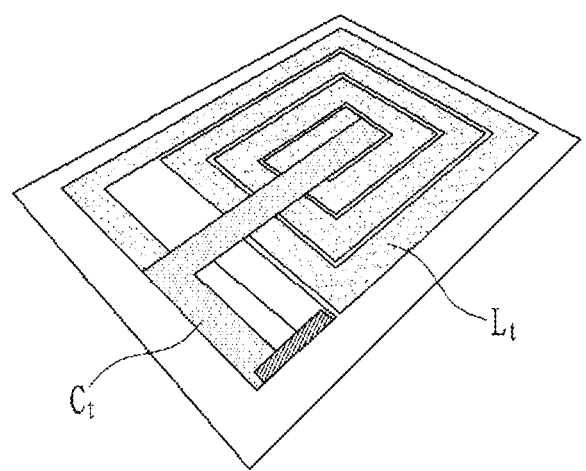
FIG. 3A is a view illustrating a shape of a capacitor according to an example embodiment.

Hereinafter, the capacitor Ct according to an example embodiment will be described with reference to FIGS. 3A and 3B. FIG. 3A illustrates a shape of the capacitor according to an example embodiment, FIG. 3B illustrates a structure of the capacitor according to an example embodiment, and FIG. 3C is a graph illustrating characteristics of the first capacitor according to an example embodiment.

The capacitor Ct may have capacitance of several pF while maintaining low electrode resistance. Referring to FIG. 3A, the capacitor Ct may be formed on the spiral inductor Lt by superimposing the stretchable electrode on a part of the spiral inductor Lt in order to allow the capacitor Ct to have low electrode resistance.

Figure 3B:
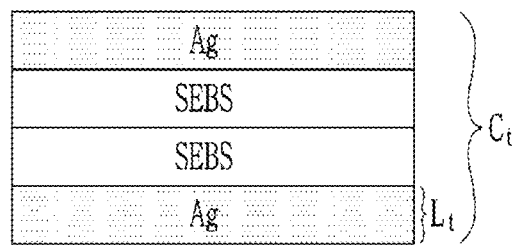
FIG. 3B is a view illustrating a structure of the capacitor according to an example embodiment.

Referring to FIG. 3B, the capacitor Ct may be formed to have a sandwich structure by superimposing the silver nano-particle stretchable electrode Ag on the spiral inductor Lt and laminating two layers of SEBS dielectric materials between the inductor Lt and the stretchable electrode Ag. The capacitor Ct having a sandwich structure may be manufactured by laminating two SEBS dielectric materials on the inductor Lt and then laminating another electrode Ag.

Figure 3C:
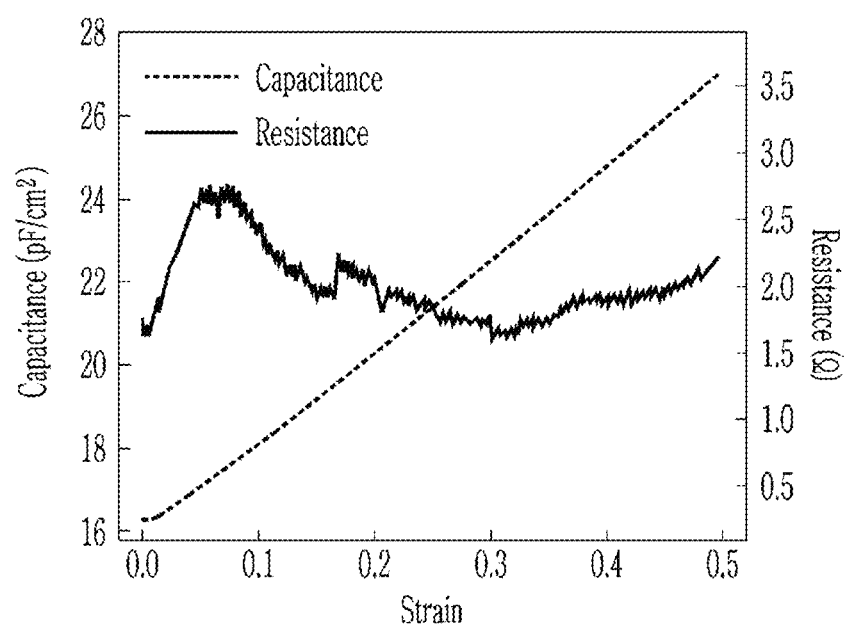
FIG. 3C is a graph illustrating characteristics of the capacitor according to an example embodiment.

Referring to FIG. 3C, in one example, the capacitor Ct has a unit capacitance of 16.3 pF/cm$^2$ in the first state of 0 strain. In the second state of 0.5 strain, an area of the electrode Ag increases and a thickness of the dielectric material SEBS decreases, such that the unit capacitance increases to 22.0 pF/cm$^2$. In this case, the resistance value of the electrode AG having the increased area is maintained as low electrode resistance, that is, a second reference resistance value (e.g., 3Ω) or less, and as a result, it is possible to successfully operate the system 1 even under a highly stretched condition.

Figure 4:
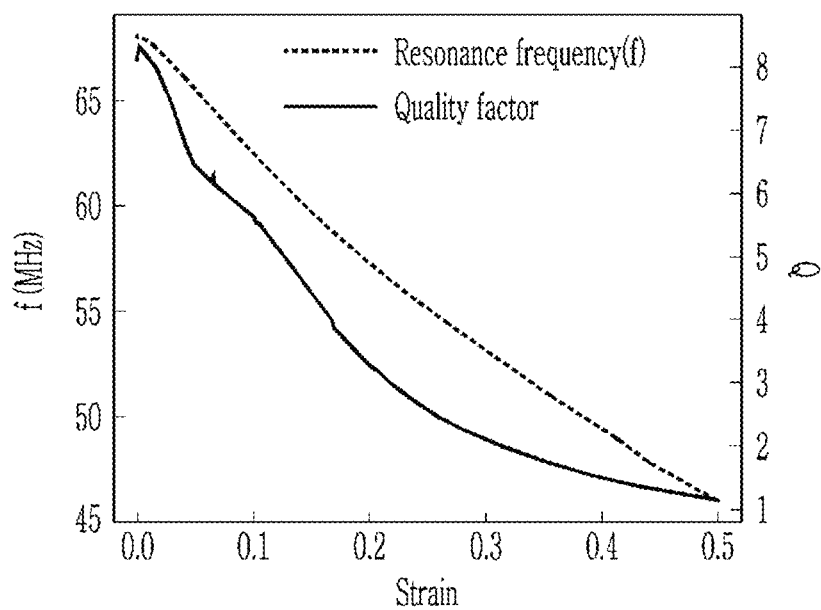
FIG. 4 is a graph illustrating characteristics of the antenna according to an example embodiment.

Hereinafter, characteristics of the antenna 11 will be described with reference to FIG. 4. FIG. 4 is a graph illustrating characteristics of the antenna according to an example embodiment.

The antenna 11 forms a resonance structure of the tag unit 10 by the inductor Lt and the capacitor Ct. The quality factor Q may be calculated by putting the inductance value illustrated in FIG. 2B and the resistance value illustrated in FIG. 3C into the aforementioned Equation 1. The resonant frequency f may be calculated by the putting the inductance value illustrated in FIG. 2B and the capacitance value in FIG. 3C into the aforementioned Equation 1.

Referring to FIG. 4, when the tag unit 10 is stretched from the first state of about 0 strain to the second state of about 0.5 strain, the natural resonant frequency f of the tag unit 10 decreases from 68.1 MHz to 46.0 MHz, and the quality factor Q decreases from 8.1 to 1.2.

The readout unit 20 is designed to accurately resonate at 13.56 MHz and at the coupling coefficient k. The design provides a desired maximum sensitivity to ensure a desired or maximum wireless operating distance.

However, a bandwidth with respect to the resonant frequency f is very narrow in a case in which only the resonant frequency of 13.56 MHz of the readout unit 20 is used, and a range of permitting a drop of the quality factor Q is narrow. That is, the quality factor Q of the antenna 11 may decrease due to an increase in parasitic resistance Rt and an increase in inductance of the inductor Lt, and as a result, the system 1 may not operate stably. In addition, when the coupling coefficient k is increased, the antenna 11 of the tag unit 10 may cause a strong loading effect to the antenna 21 of the readout unit 20, and as a result, the sensitivity S (see FIG. 5A) of the antenna 11 may rapidly decrease.

Therefore, to solve the aforementioned problem, it is necessary to design the antenna 11 that operates within other resonant frequency regions other than 13.56 MHz in the related art.

The readout unit 20 according to an example embodiment operates at the resonant frequency of 13.56 MHz, and the tag unit 10 may operate within other frequency regions other than the resonant frequency of 13.56 MHz even in the first state as well as the second state in which the coupling coefficient k is high.

Figure 5A:
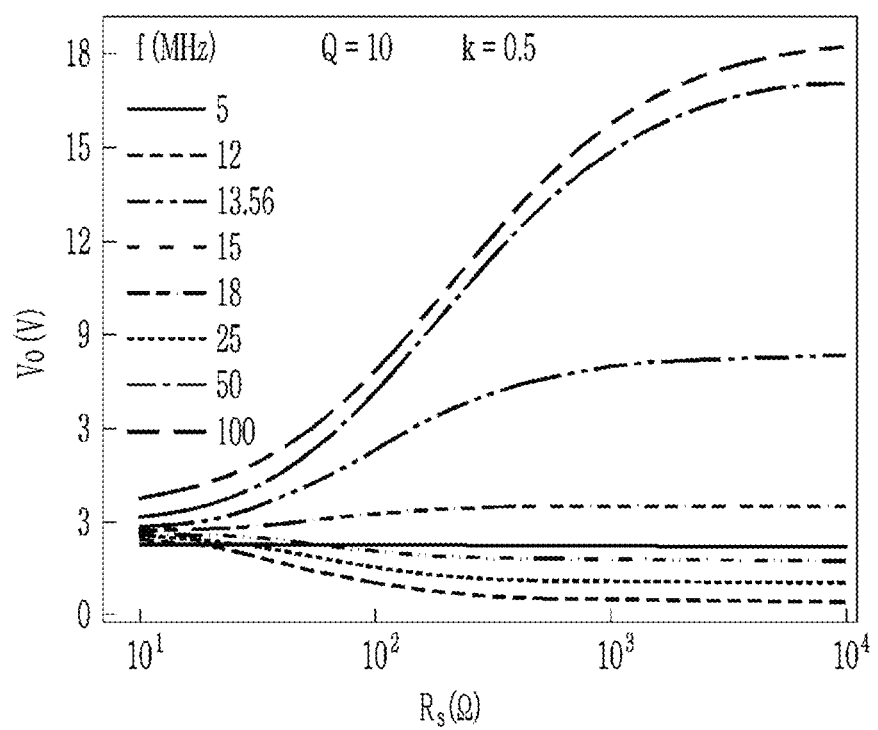
FIG. 5A is a graph illustrating output voltages in accordance with resonant frequencies.
Figure 5B:
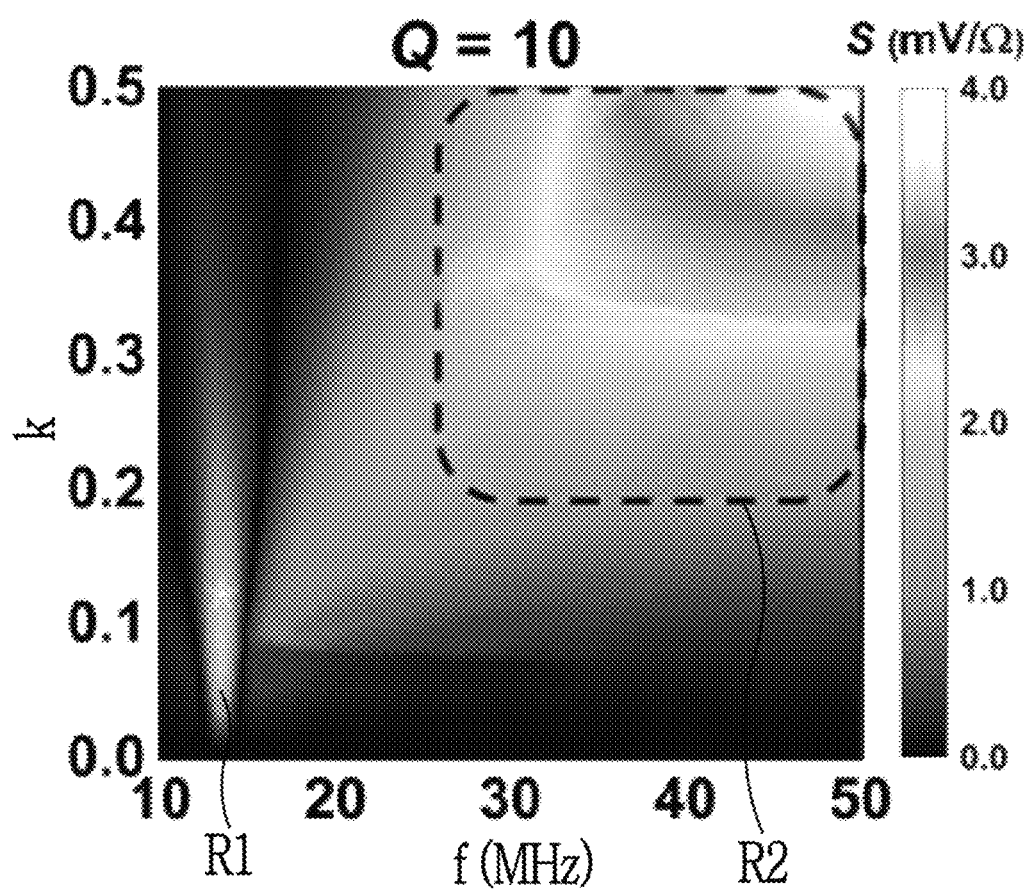
FIG. 5B is a graph illustrating an operating region of the system according to an example embodiment.
Figure 5C:
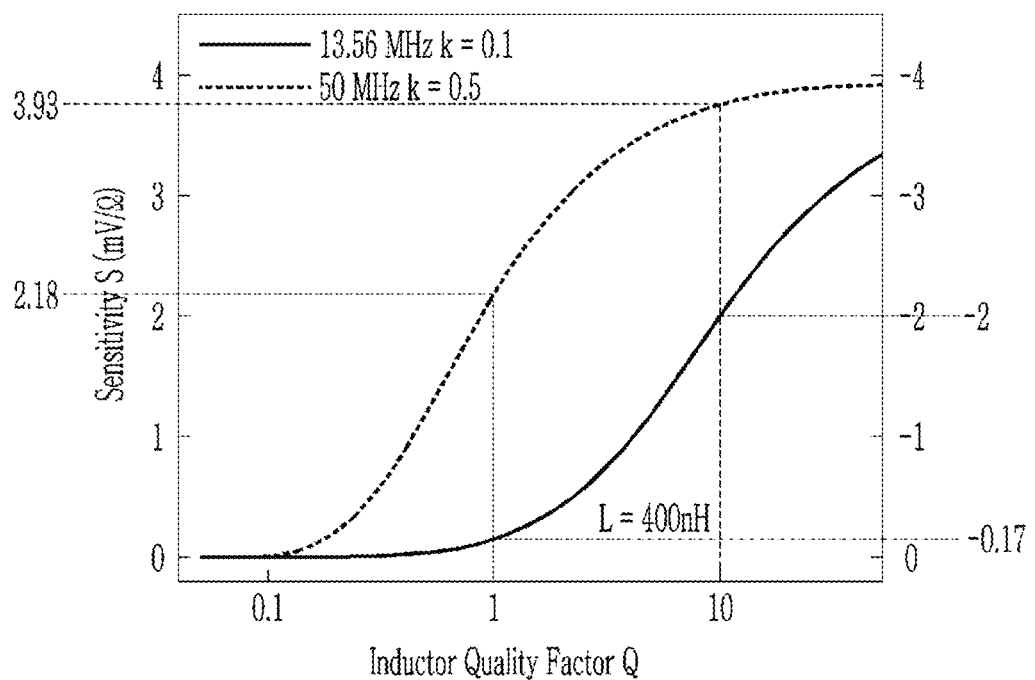
FIG. 5C is a graph illustrating sensitivity of the system in accordance with a change in quality factor in each region.

Hereinafter, the operating regions of the tag unit 10 and the readout unit 20 according to an example embodiment will be specifically described with reference to FIG. 5. FIG. 5A is a graph illustrating output voltages Vo in accordance with the resonant frequencies f. FIG. 5B is a graph illustrating the operating region of the system according to an example embodiment. FIG. 5C is a graph illustrating the sensitivity S of the system in accordance with a change in coupling coefficient k within each region.

Referring to FIG. 5A, assuming that a rate of change in output voltage Vo (e.g., a gradient of the graph in FIG. 5A) when k=0.5 and Q=10 is defined as the sensitivity S, the gradient of the graph is rapid in a section in which the resistance Rs of the sensor 12 is 10$^2$Ω to 10$^3$Ω in a case in which the resonant frequency f is accurately 13.56 MHz, or is 50 MHz or 100 MHz greater than 30 MHz; thus, the sensitivity S is high when the resonant frequency f is 13.56 MHz, 50 MHz, or 100 MHz.

Specifically, referring to FIG. 5B, when the resistance Rs of the sensor is 700Ω, the readout unit 20 may operate in a first region R1, and the tag unit 10 may operate in a second region R2.

The first region R1 is a region that corresponds to a low coupling coefficient k (0.1 or less) and the resonant frequency f of 13.56 MHz. In addition, the first region R1 is a region in which the sensitivity S is greatly changed in response to a small change in resonant frequency fin accordance with the stretch.

The second region R2 is a region that corresponds to a high k value (0.2 or more) and a resonant frequency f of 30 MHz to 50 MHz, and a region in which the sensitivity S may be maintained at a high level even though the resonant frequency f is changed.

In addition, the second region R2 has a wide range of permitting a drop of the quality factor Q. Specifically, referring to FIG. 5C, when the quality factor Q is decreased from 10 to 1, the sensitivity S in the second region R2 is decreased from 3.93 mV/Ω to 2.18 mV/Ω, while the sensitivity S in the first region R1 is rapidly decreased from −2 V/Ω to −0.17 mV/Ω. Therefore, even though the quality factor Q may change greatly in the second region R2, the change in sensitivity S is smaller in the second region R2 than in the first region R1.

Referring back to FIG. 4, when the tag unit 10 changes from the first state to the second state, the resonant frequency f of the tag unit 10 changes from 68.1 MHz to 46.0 MHz. In this case, since the sensitivity S in the second region R2 slowly decreases from 3.93 mV/Ω to 2.18 mV/Ω even though the quality factor Q greatly decreases from 8.1 to 1.2, the change in sensitivity S is small even though the change in quality factor Q is large.

In addition, since the resonant frequency f of the second region R2 is 30 MHz or more and thus high, a capacitance value of the capacitor Ct may not be a large value. Therefore, the electrode Ag that forms the capacitor Ct no longer has to be thin and may be easier to manufacture. Also, the reliability may be improved because the change in sensitivity S is small even when the sensor is stretched.

Figure 6A:
FIG. 6A is a view illustrating a sensor according to an example embodiment.
Figure 6B:
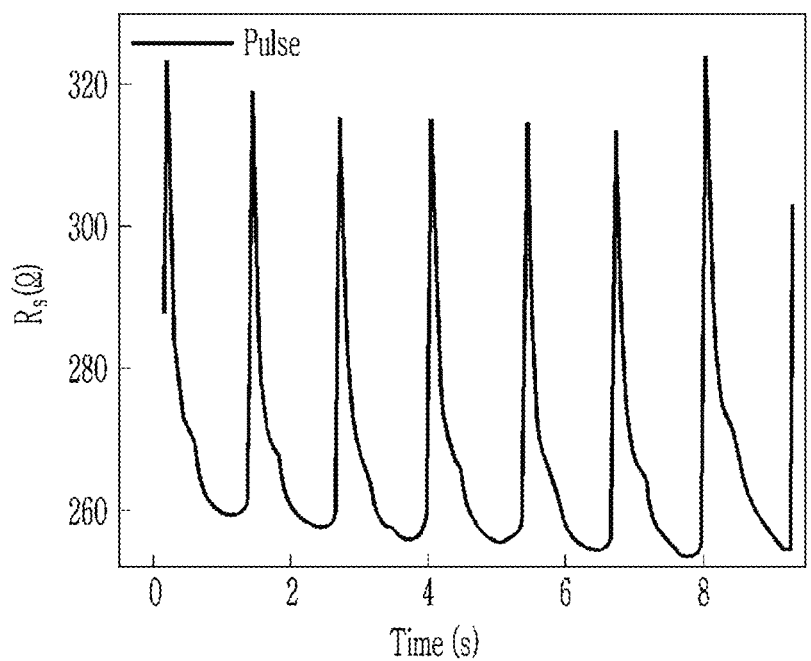
FIG. 6B is a graph illustrating characteristics of the sensor according to an example embodiment.

Hereinafter, the sensor according to an example embodiment will be described with reference to FIGS. 1, 5A, and 6. FIG. 6A illustrates the sensor according to an example embodiment, and FIG. 6B is a graph illustrating characteristics of the sensor according to an example embodiment.

Referring to FIGS. 1 and 6A, the sensor 12 may be a resistive strain sensor that is attachable to the skin. The sensor 12 may include the resistor Rs and may include one or more carbon nanotubes (CNTs) embedded in polydimethylsiloxane (PDMS), and the sensor 12 may be a stretchable sensor made based on a coffee ring effect.

The sensor 12 attached to the skin creates a sensing signal caused by amplitude modulation corresponding to the degree of stretching of the resistor Rs. As described above, the readout unit 20 reads out the sensing signal of the tag unit 10 by using amplitude of the output voltage Vo corresponding to the received sensing signal.

The sensor 12 may be designed to have high sensitivity S. In some embodiments, a value of the resistor Rs may be smaller than a third reference resistance (e.g., 103Ω) in the first state.

FIG. 6B illustrates resistance values of the resistor Rs in accordance with measurement time in a case in which the sensor 12 is a heart rate sensor. The sensor 12 is stretched corresponding to the heart rate, and as a result, the resistance values of the resistor Rs have a pulse shape. The sensing signal is created from the tag unit 10 by load modulation corresponding to the pulse shape, and the readout unit 20 reads out the sensing signal by using amplitude of the output voltage Vo corresponding to the sensing signal.

For ease of description, the configuration in which the sensor 12 is the heart rate sensor has been described, but an example embodiment is not limited thereto, and any sensor may be included as long as the sensor is a sensor for detecting biological signals of humans such as breathing and body motion by using stretchable resistors.

Hereinafter, characteristics of the system 1 in accordance with the degrees of stretching of the tag unit 10 according to an example embodiment and distances between the tag unit 10 and the readout unit 20 will be described with reference to FIGS. 7A to 7D.

Figure 7A:
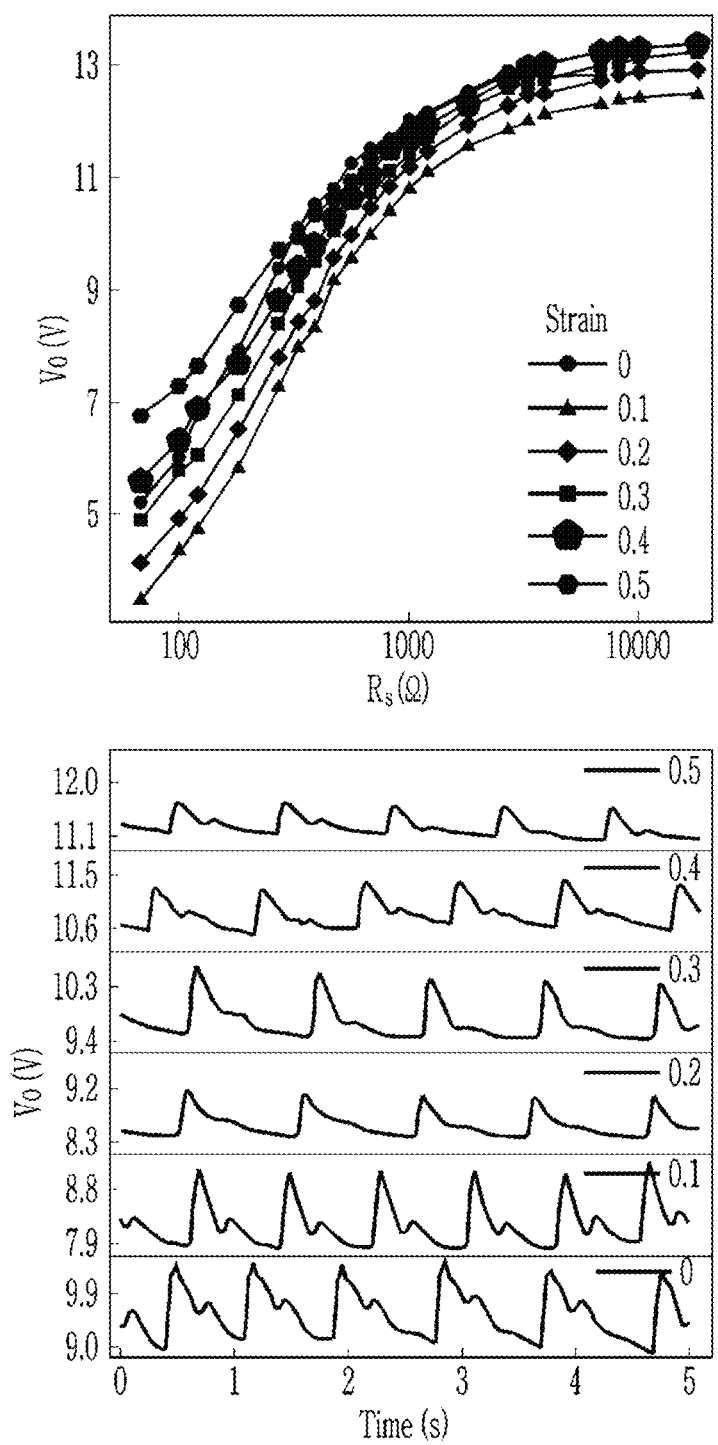
FIG. 7A is a graph illustrating output voltages in accordance with degrees of stretching of a tag unit according to an example embodiment.
Figure 7B:
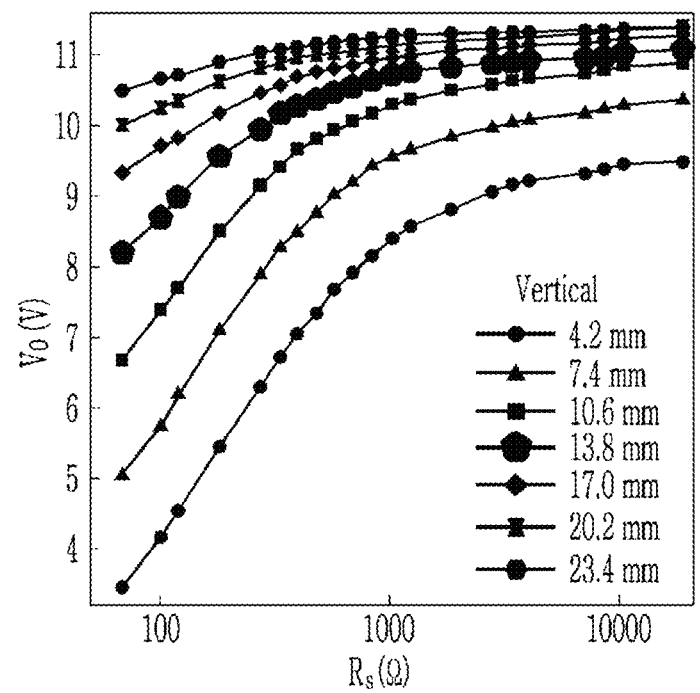
FIG. 7B is a graph illustrating output voltages in accordance with horizontal distances between the tag unit and a readout unit according to an example embodiment.
Figure 7B:
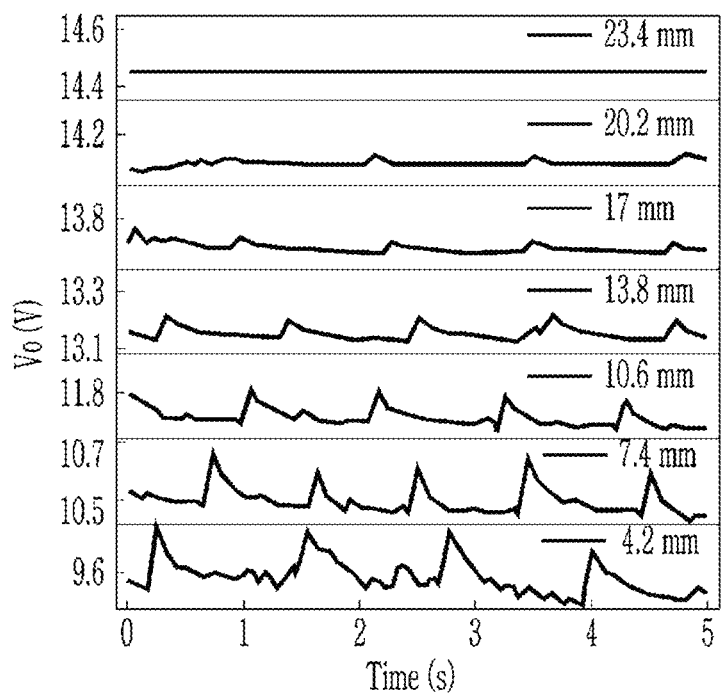

FIG. 7A is a graph illustrating output voltages in accordance with degrees of stretching of the tag unit according to an example embodiment, and FIG. 7B is a graph illustrating output voltages in accordance with horizontal distances between the tag unit and the readout unit according to an example embodiment.

Figure 7C:
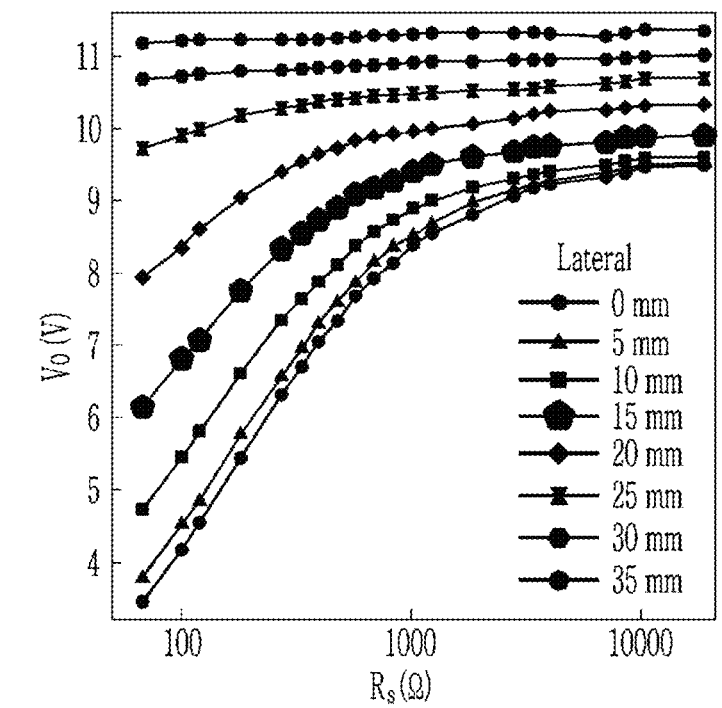
FIG. 7C is a graph illustrating output voltages in accordance with vertical distances between the tag unit and the readout unit according to an example embodiment.
Figure 7C:
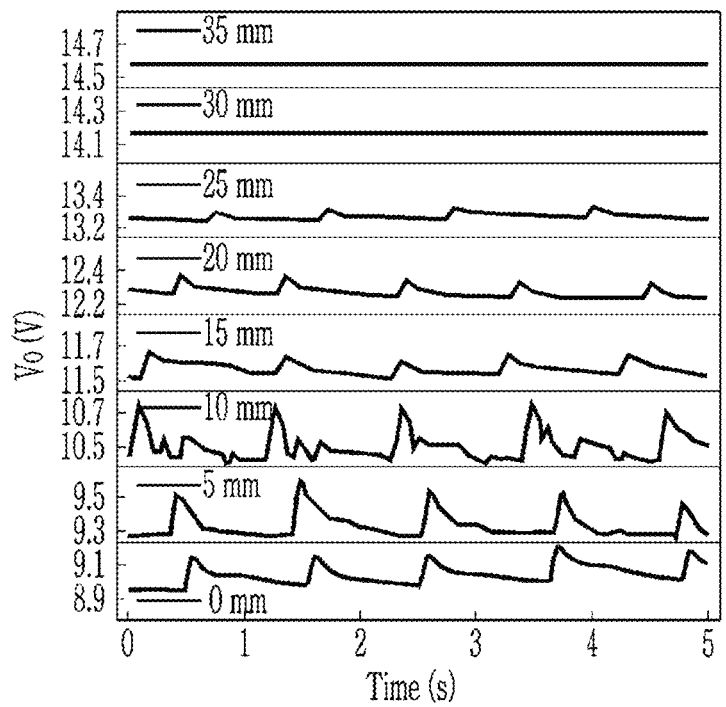

FIG. 7C is a graph illustrating output voltages in accordance with vertical distances between the tag unit and the readout unit according to an example embodiment.

Referring to FIGS. 1 and 7A, the sensitivity S (which corresponds to the gradient of the graph) is maintained to have a very large value until the resistor Rs is changed from the first state to the second state in a section in which the resistance value of the resistor Rs is the third reference resistance (103Ω) or less. In addition, a biological pulse signal of a human may be detected as an output voltage Vo corresponding to the biological pulse signal of the human even though the resistor Rs is changed from the first state to the second state. Therefore, the system 1 according to an example embodiment may detect the biological signal of the human even though the tag unit 10 is in the second state.

Referring to FIGS. 1 and 7B, as the vertical distance between the tag unit 10 and the readout unit 20 increases from 4.2 mm, the sensitivity S (which corresponds to a gradient of a curve in FIG. 7B) is increased and then rapidly decreased in the section in which the resistance value of the resistor Rs is the third reference resistance (103Ω) or less. When the vertical distance exceeds 20 mm, the curve becomes approximately flat, and the sensitivity S becomes close to 0. That is, a peak of the output voltage Vo is highest when the vertical distance is 4.2 mm, and the output voltage Vo is rarely detected when the vertical separation distance exceeds 20 mm and reaches 23.4 mm.

Referring to FIG. 7C, as the horizontal (or lateral) distance between the tag unit 10 and the readout unit 20 increases from 0 mm, the sensitivity S is increased and then rapidly decreased in the section in which the resistance value of the resistor Rs is the third reference resistance (103Ω) or less. When the horizontal distance exceeds 25 mm, the curve becomes approximately flat, and the sensitivity S becomes close to 0. That is, the peak of the output voltage Vo is highest when the horizontal distance is 0 mm, and the output voltage Vo is rarely detected when the horizontal separation distance exceeds 25 mm and reaches 35 mm.

Figure 8:
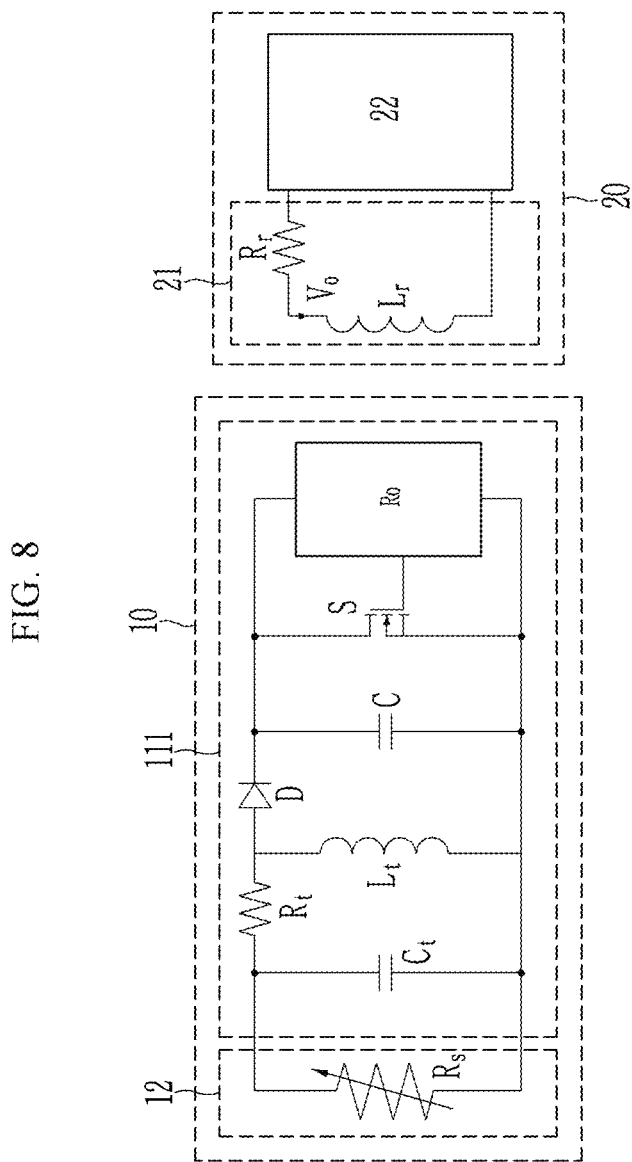
FIG. 8 is a view illustrating a specific configuration of an sensor system according to an example embodiment.

Hereinafter, a sensor system according to an example embodiment will be described with reference to FIGS. 1 and 8. FIG. 8 illustrates a specific configuration of the sensor system according to an example embodiment.

Referring to FIG. 8, the antenna 111 includes a stretchable diode D1 (hereinafter, referred to as the diode), a capacitor C, a stretchable transistor S (hereinafter, referred to as the transistor), and a stretchable ring oscillator Ro (hereinafter, referred to as the ring oscillator) in addition to the inductor Lt, the capacitor Ct, and the parasitic resistance Rt illustrated in FIG. 1, and the antenna 111 may be connected to the sensor 12.

Because the inductor Lt, the capacitor Ct, the parasitic resistance Rt, and the sensor 12 are identical to those described with reference to FIG. 1, detailed descriptions thereof will be omitted.

The diode D rectifies a wireless power signal which is transmitted from the readout unit 20 and corresponds to the second region. To this end, an operating frequency of the diode D may be 100 MHz or more, a breakdown voltage thereof may be 50 V or more, a reverse leakage current thereof may be smaller than 100 nA, and a forward current thereof may be 0.1 mA or more. To implement the features, the diode D1 may have, but not limited to, a metal-semiconductor Schottky structure.

The capacitor C stores energy corresponding to the signal rectified by the diode D, and the stored energy may be used as power for operating the ring oscillator Ro.

The transistor S may be a transistor controlled by the ring oscillator Ro and used for load modulation.

The ring oscillator Ro may have an inherent operating frequency range and modulates a frequency of the sensing signal in accordance with a degree of stretching of the antenna 111. The operating frequency of the ring oscillator Ro may be changed in accordance with the degree of stretching of the resistor Rs, and the modulated sensing signal may be created corresponding to the change in operating frequency of the ring oscillator Ro. The modulated sensing signal is transmitted to the readout unit 20 through the antenna 111.

Because the ring oscillator Ro uses RF harvested energy, a low operating voltage (e.g., lower than 15 V), a low power consumption (e.g., less than 1 mW), and a wide frequency region (e.g., exceeding 100 Hz) may be required.

Multiple tag units, which include multiple sensors and multiple ring oscillators corresponding to the multiple sensors, may be configured to monitor multiple body signals by using multiple sensors.

For example, to monitor a heat rate, a breathing rate, and a body motion, three tag units may be attached to corresponding positions on the human body. The three tag units may include a heart rate sensor, a breathing rate sensor, a body motion sensor, and three ring oscillators matching with these sensors for monitoring the heart rate, the breathing rate, and the body motion. The three ring oscillators have may operating frequency ranges that do not overlap with each other such as 20 to 40 Hz, 70 to 100 Hz, and 300 to 500 Hz.

The readout units 20 may include an algorithm and band-pass filters corresponding to 20 to 40 Hz, 70 to 100 Hz, and 300 to 500 Hz, and may distinguish and read out modulated sensing signals corresponding to the operating frequency bands of the ring oscillators by using the algorithm and the band-pass filters.

Figure 9:
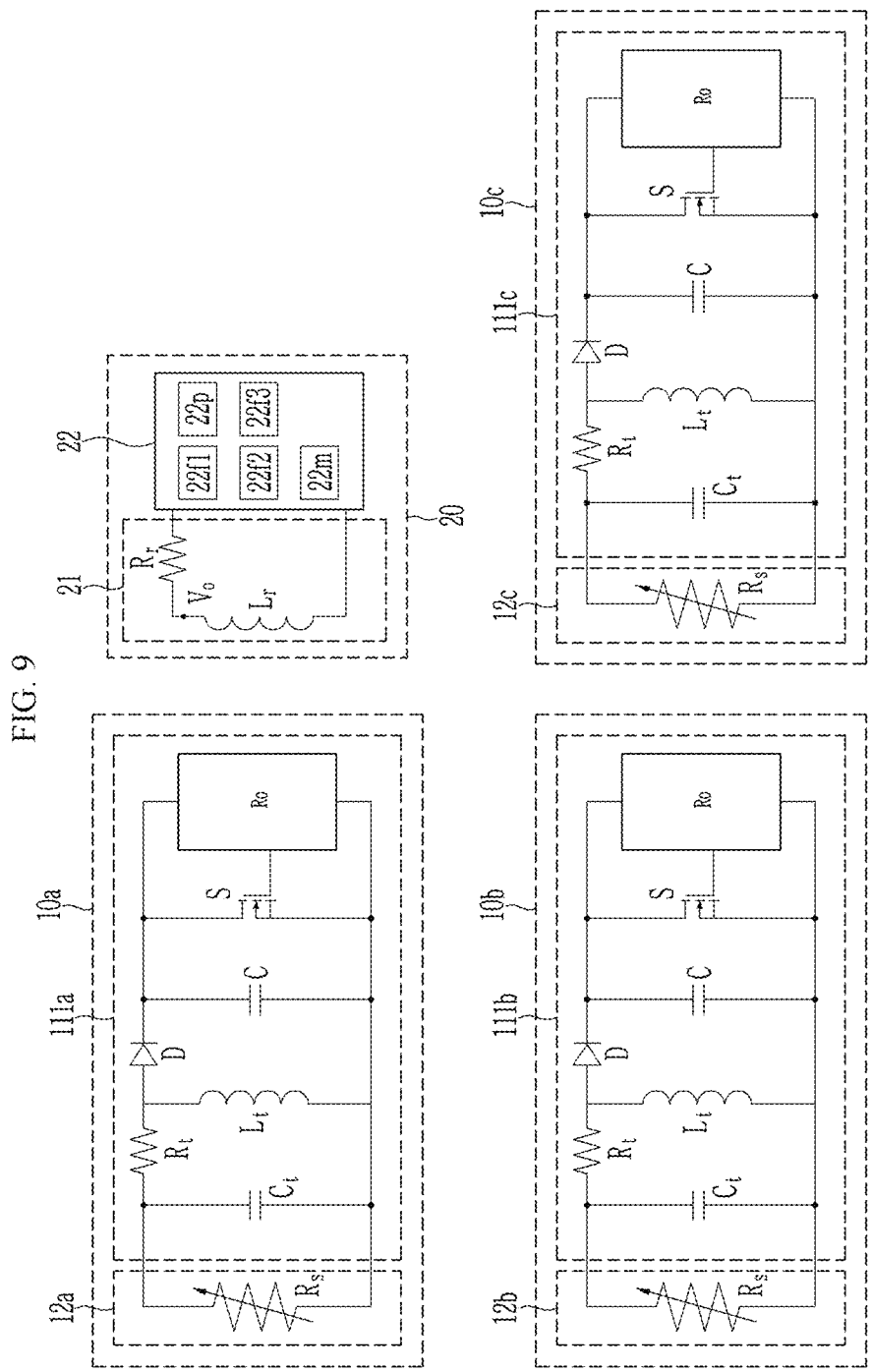
FIG. 9 is a view illustrating a specific configuration of an sensor system according to other example embodiment.

Hereinafter a sensor system according to other example embodiment will be described with reference to FIG. 9. FIG. 9 illustrates a specific configuration of a sensor system according to other example embodiment.

FIG. 9 is a diagram of a sensor system that includes a first tag unit 10a, a second tag unit 10b, a third tag unit 10c, and a readout unit 20. The first tag unit 10a, second tag unit 10b, and third tag unit 10c respectively include a stretchable sensor (e.g., 12a, 12b, and 12c) and an antenna (e.g., 111a, 111b, and 111c), which may be the same as or similar to the stretchable sensor 12 in FIG. 1 and the antenna 111 in FIG. 8. The tag units 10a, 10b, and 10c may monitor different parts of the body and may correspond to a heart rate monitor, a breathing monitor, and a body motion monitor, but are not limited thereto.

The readout unit 20 may be the same as the readout unit 20 in FIG. 1, except the circuit unit 22 further includes first to third band-pass filter circuits 22f1, 22f2, and 22f3 that operate a different frequencies; a multiple-band processing circuit 22p; and a memory 22m. The memory 22m may include instructions, such as a signal-processing algorithm, that when executed by the processing circuit 22p configure that readout unit 20 to distinguish signals sensed from the first tag unit 10a, second tag unit 10b, and third tag unit 10c from each other.

While some example embodiments have been particularly shown and described, it will be understood by one of ordinary skill in the art that variations in form and detail may be made therein without departing from the spirit and scope of the claims.

What is claimed is:

1. A sensor system comprising:
a tag unit,
the tag unit including a first sensor,
the first sensor including a stretchable antenna and a stretchable resistor,
the tag unit being configured to create a sensing signal corresponding to a degree of stretching of the stretchable resistor, transmit the sensing signal to a readout unit through the stretchable antenna, and operate in a first region corresponding to a first frequency, the first frequency being in a range from 30 MHz to 50 MHz; and
the readout unit, which is inductively-coupled to the tag unit,
the readout unit being configured to receive and read out the sensing signal and operate in a second region corresponding to a second frequency,
the second frequency being different from the first frequency.

2. The sensor system of claim 1, wherein:
the second frequency is 13.56 MHz,
the first region is a region corresponding to the first frequency and a first coupling coefficient,
the second region is a region corresponding to the second frequency and a second coupling coefficient, and
the first coupling coefficient is greater than the second coupling coefficient.

3. The sensor system of claim 2, wherein:
the stretchable antenna includes stretchable electrodes that form an inductor and a first capacitor,
the stretchable electrodes include a first stretchable electrode and a second stretchable electrode,
the second stretchable electrode overlaps a part of the inductor,
the inductor includes the first stretchable electrode,
the inductor has a spiral shape where the first stretchable electrode is arranged in the spiral shape,
the first capacitor includes the second stretchable electrode, and
the inductor and the first capacitor are configured to be stretched from a first state to a second state that is different than the first state.

4. The sensor system of claim 3, wherein:
in the second state, a resistance value of the first stretchable electrode is a first reference resistance value or less, and
in the second state, a resistance value of the second stretchable electrode is a second reference resistance value or less.

5. The sensor system of claim 4, wherein:
in the first state, a resistance value of the stretchable, resistor is a third reference resistance value or less.

6. The sensor system of claim 5, wherein:
the first reference resistance value, the second reference resistance value, and the third reference resistance value are 100Ω, 3Ω, and 1,000Ω, respectively.

7. The sensor system of claim 6, wherein:
the first capacitor has a sandwich structure in which a dielectric material is included between a part of the inductor and the second stretchable electrode, and
a conductivity of each of the first stretchable electrode anti the second stretchable electrode is lower than 0.05 Ohm/square.

8. The sensor system of claim 7, wherein:
the sandwich structure includes two styrene-ethylene-butylene-styrene (SEBS) dielectric materials.

9. The sensor system of claim 8, wherein:
the inductor has an inductance of 451.5 nH and a resistance value of 2.98Ω in the first state, and
the inductor has an inductance of 595.2 rill and a resistance value of 41.7Ω in the second state.

10. The sensor system of claim 9, wherein:
a unit capacitance of the first capacitor is 16.3 pF/cm$^2$ in the first: state and 22.0 pF/cm$^2$ in the second state.

11. The sensor system of claim 10, wherein:
the first sensor is a resistive strain sensor,
the first sensor is configured to attach to skin, and
the first sensor includes one or more carbon nanotubes.

12. The sensor system of claim 11, wherein:
the first state is anon-stretched state, and
the second state is a state further stretched by 50% than the first state.

13. The sensor system of claim 12, wherein:
the stretchable antenna further includes a diode, a second capacitor, and a first ring oscillator having a first operating frequency range,
the diode is configured to rectify a wireless power signal corresponding to the second region to provide a rectified wireless power signal,
the second capacitor is configured to store energy corresponding to the rectified wireless power signal,
the first ring oscillator is configured to use energy stored in the second capacitor and create a first modulated sensing signal by modulating a frequency of the sensing signal in accordance with the degree of stretching of the first sensor within the first operating frequency range, and
the readout, unit is configured to read out the first modulated sensing signal.

14. The sensor system of claim 13, wherein:
the antenna further includes a second sensor, and a second ring oscillator having a second operating frequency range,
the second ring oscillator is configured to create a second modulated sensing signal by modulating a frequency of the sensing signal in accordance with a degree of stretching of the second sensor within the second operating frequency range,
the first sensor and the first ring oscillator match with each other, the second sensor and the second ring oscillator match with each other, and the first operating frequency range and the second operating frequency range are different from each other.

15. The sensor system of claim 14, wherein:
the readout unit is configured to distinguish and read out the first modulated sensing signal and the second modulated sensing signal.

16. The sensor system of claim 15, wherein:
the readout unit includes a first band-pass filter and a second band-pass filter,
the first band-pass filter corresponds to the first operating frequency range,
the second band-pass filter corresponds to the second operating frequency range, and
the readout unit configured to distinguish and read out the first modulated sensing signal and the second modulated sensing signal by using the first band-pass filter and the second band-pass filter.

17. The sensor s stem of claim 16, wherein:
the diode has metal-semiconductor Schottky structure.

18. The sensor system of claim 17, wherein:
the diode, the second capacitor, the second sensor, the first ring oscillator, and the second ring oscillator all include stretchable materials.

19. The sensor system of claim 5, wherein:
the second reference resistance value is greater than the first reference resistance value and less than the third reference resistance value.

20. The sensor system of claim 8, wherein:
the first state is a non-stretched state,
the second state is a stretched state,
the inductor has a first inductance value and a first resistance value in the first state,
the inductor has a second inductance value and a second resistance value in the second state,
the second inductance value is greater than the first inductance value, and
the second resistance value is greater than the first resistance value.

\* \* \* \* \*